(12) United States Patent
Stiffey-Wilusz

(10) Patent No.: US 6,468,735 B2
(45) Date of Patent: Oct. 22, 2002

(54) ANGIOGENESIS ASSAY

(75) Inventor: Janet Stiffey-Wilusz, Pittstown, NJ (US)

(73) Assignee: Merck & Co., Inc., Rahway, NJ (US)

(*) Notice: Subject to any disclaimer, the term of this patent is extended or adjusted under 35 U.S.C. 154(b) by 48 days.

(21) Appl. No.: 09/793,647

(22) Filed: Feb. 26, 2001

(65) Prior Publication Data

US 2001/0046666 A1 Nov. 29, 2001

Related U.S. Application Data

(60) Provisional application No. 60/193,840, filed on Mar. 31, 2000.

(51) Int. Cl.[7] .............................. C12Q 1/00; C12Q 1/02; C12Q 1/04
(52) U.S. Cl. ................................ 435/4; 435/29; 435/34; 435/975; 435/283.1
(58) Field of Search .............................. 435/4, 29, 34, 435/975, 283.1

(56) References Cited

U.S. PATENT DOCUMENTS 6,114,355 A * 9/2000 D'Amato .................... 514/323
6,203,556 B1 * 3/2001 Evans et al. ................ 606/185
6,242,481 B1 * 6/2001 Udagawa et al. ........... 514/468

OTHER PUBLICATIONS

Laboratory Investigation, vol. 75, No. 4, pp. 539–555 (1996), by K. J. Brown, et al.
In Vitro, vol. 18, No. 6, pp. 538–549 (1982), by R. F. Nicosia, et al.

* cited by examiner

*Primary Examiner*—Louise N. Leary
(74) *Attorney, Agent, or Firm*—Dianne Brown; Mark R. Daniel

(57) ABSTRACT

The present invention relates to assays and kits using porcine carotid arteries for screening compounds to identify modulators of angiogenesis. In particular, an assay for rapidly screening compounds that inhibit angiogenesis is provided.

11 Claims, No Drawings

ANGIOGENESIS ASSAY

This application claims the benefit of Provisional application Ser. No. 60/193,840, filed Mar. 31, 2000.

BACKGROUND OF THE INVENTION

The present invention relates to assays and kits using porcine carotid arteries for screening compounds to identify modulators of angiogenesis. In particular, an assay for rapidly screening compounds that inhibit angiogenesis is provided.

Angiogenesis is normally observed in wound healing, fetal and embryonal development and formation of the corpus luteum, endometrium and placenta. The control of angiogenesis is a highly regulated system of angiogenic stimulators and inhibitors. Thus, angiogenesis is a critical component of the body's normal physiology, especially during wound healing.

In addition, the control of angiogenesis has been found to be altered in certain disease states, and, in many cases, the pathological damage associated with the disease is related to the uncontrolled angiogenesis. It also has a detrimental aspect, for example, when blood vessels multiply and enhance growth and metastasis of tumors. Aberrant angiogenesis is also associated with numerous disorders, including rheumatoid arthritis, where blood vessels invade the joint and destroy cartilage, and numerous ophthalmologic pathologies, such as diabetic retinopathies in which new capillaries invade the vitreous, bleed and cause blindness, and macular degeneration, prostate cancer and Kaposi's carcinoma. Angiogenesis is essential to tumor development and growth. Prevention of angiogenesis can inhibit solid tumor growth.

Compounds that have anti-angiogenic activity can be used, for example, as anti-tumor agents and for the treatment of ophthalmic disorders, particularly involving the retina and vitreous humor, and for hyperproliferative dermatological disorders, such as psoriasis, that have an angiogenic component. Thus, compounds that enhance angiogenesis and compounds that inhibit angiogenesis are being sought.

This has led to a search for specific inhibitors of endothelial cell growth. As a result, there is an interest in measuring proliferation of endothelial cells under inhibitory and stimulatory conditions as screens for discovery of inhibitors (or alternatively stimulators) of angiogenesis.

Direct assessment of cell numbers, either microscopically or by particle counter is time consuming and not amenable for high throughput screening. Consequently, direct assessment has been replaced by indirect methods, such as by packed cell volume, by chemical determination of a cellular component, for example, protein or deoxyribonucleic acid, or by uptake of a chromogenic dye such as neutral red.

These methods can be laborious when handling large numbers of cultures, and also inaccurate at low cell densities. For high throughput screening protocols it is necessary to rapidly and accurately measure low cell densities and/or relatively small changes in cell number over a large range of cell densities. Presently available protocols to not provide a means to do this. Thus, there is a need for convenient, rapid and reproducible assays for identifying agents that modulate angiogenesis.

Therefore it is an object herein to provide a method for identifying compounds that modulate angiogenesis. In particular, it is an object herein to provide a method of screening for inhibitors of angiogenesis.

SUMMARY OF THE INVENTION

The present invention relates to assays and kits using porcine carotid arteries for screening compounds to identify modulators of angiogenesis. In particular, an assay for rapidly screening compounds that inhibit angiogenesis is provided.

DETAILED DESCRIPTION OF THE INVENTION

A first embodiment of the present invention is illustrated by a method of analyzing the angiogenesis modulating effect of a compound, comprising the steps of:
 (a) incubating a sample comprised of a fragment of porcine carotid artery with the compound;
 (b) generating images of the sample; and
 (c) quantitating the images to determine the extent of angiogenesis.

In a second embodiment, the incubation of step (a) is done in a humidified atmosphere of about 5% carbon dioxide at about 30° C. to about 40° C. for about 1 to 4 weeks.

In yet another embodiment, the incubation of step (a) is done in a humidified atmosphere of about 5% carbon dioxide at about 37° C. for about 2 to 3 weeks.

The process wherein the incubation of step (a) is done using Matrigel™ as the matrix is yet one more embodiment.

Also encompassed by the present invention is the method described above wherein the images generated in step (b) are digital.

In still another embodiment, the digital images are quantitated in step (c) using image analysis software.

Another embodiment is the method described above wherein the digital images are quantitated in step (c) using image analysis software and the vessel body is subtracted out of the pixel calculation.

A preferred embodiment is a method of analyzing the angiogenesis modulating effect of a compound, comprising the steps of:
 (a) incubating a sample comprised of a fragment of porcine carotid artery with the compound in a humidified atmosphere of about 5% carbon dioxide at about 37° C. for about 2 to 3 weeks;
 (b) generating digital images of the sample; and
 (c) quantitating the digital images to determine the extent of angiogenesis by using image analysis software.

A subembodiment of the present invention is the method described above wherein the angiogenesis modulating effect is inhibition of angiogenesis.

Another embodiment is a method of analyzing the angiogenesis inhibiting effect of a compound, comprising the steps of:
 (a) incubating a sample comprised of a fragment of porcine arotid artery with the compound in a humidified atmosphere of about 5% carbon dioxide at about 37° C. for about 2 to 3 weeks in a Matrigel™ matrix;
 (b) generating digital images of the sample; and
 (c) quantitating the digital images to determine the extent of angiogenesis by using image analysis software.

Also encompassed by the instant claims is a kit for analyzing the angiogenesis modulating effect of a compound, comprising a fragment of porcine carotid artery in a medium with sufficient nutrients to allow growth of new vascular tissue.

In the claims, "porcine carotid artery" refers to blood vessels from both adult and fetal animals.

The study of angiogenesis as a therapeutic target requires a reliable, physiologically relevant, and technically straightforward assay. An ex vivo assay bridges the gap between cell-based assays, which may not realistically represent the complex process of vessel sprouting, and in vivo assays, which are time consuming and expensive. Porcine carotid arteries provide an ideal tissue source for angiogenesis inhibitor screens due to their availability, physiological relevance and large size. The present assay has numerous advantages over the rat aortic ring assay (Nicosia, R. F., et al, *In Vitro*. 18:538–549). Among these advantages is that it reduces the number of animals used, increases reproducibility (decreased animal-to-animal variability), decreases costs by eliminating need to house animals since tissue source is commercially available, and increases productivity.

Angiogenesis is a complex biological process which is the result of a variety of cellular interactions. Tissue fragments growing in a three-dimensional matrix provide a model system for the study of angiogenic processes with a complete source of relevant cell types. Evaluation of angiogenic compounds is a difficult process and often requires a variety of assays to determine the potential of a given compound as a therapeutic agent. An assay that is often used to evaluate angiogenesis is the aortic ring assay as mentioned above. Although this assay addresses the complexity of cell-type interactions, it has numerous disadvantages including animal to animal variability.

By purchasing blood vessels from an abattoir, many issues associated with the use of research animals are avoided. Not only is the number of animals used per assay reduced, but need to house research animals is also eliminated. This creates both social and economic savings. Due to the close approximation of porcine to human vasculature, adult porcine carotid arteries serve as the most useful source of tissue for this relatively high throughput assay.

If only a small number of compounds are to be tested, fetal porcine carotid arteries may be more appropriate; their sterility, shorter growth time, and lack of fascia make them ideal. In order to semi-automate the assay using adult porcine carotid arteries, several options must be considered. Cutting methods should incorporate a pushing or pressing motion, as opposed to a tearing method and an automatic tissue cutter would be useful for making uniform pieces of tissue. This will aid in the imaging process. The dosing regimen should be investigated to best suit the facilities available; if there are time constraints or sample limitations, the dosing schedule can be somewhat reduced. Reagents must be sterile when dosing, although the assay setup can be done on a bench top.

The recommended matrix, Matrigel™, is a trademark of Becton Dickinson Labware. Matrigel™ is isolated from the EHS mouse sarcoma (See U.S. Pat. No. 4,829,000, herein incorporated by reference). It is composed of laminin, collagen IV, entactin, and heparan sulfate proteoglycan. It also contains growth factors, matrix metalloproteinases, and other components.

The use of Matrigel™ as the matrix has both advantages and disadvantages. Matrigel™ does not solidify as rapidly as fibrin or collagen, so it is technically easier to manipulate. However, it is more expensive than either fibrin or collagen and contains growth factors. RGF Matrigel™ (reduced growth factor) is recommended because the growth factors are kept to a minimum, but it is still difficult to control for the exact amount of growth factors present. Variability is mitigated by using Matrigel™ from the same lot.

In order to get statistically relevant data, at least six replicates should be run (one row of the 48 well plate). Twenty plates worth of tissue can generally be obtained from one adult porcine carotid artery, or approximately eighty samples per assay. The assay tolerates up to 0.5% dimethylsulfoxide, and thus is suitable for compound screening. Known angiogenesis inhibitors can be detected and activity can be statistically quantified.

In this assay, the major stimulant of control growth is by bFGF (found in bovine brain extract). By manipulating growth conditions, such as growth factor stimulants and oxygen content during incubation, the assay may be adapted to other uses, as will be apparent to those skilled in the art.

EXAMPLE

Tissue Selection and Preparation

Porcine carotid arteries were purchased from Bioreclamation (Hicksville, N.Y.). In a generally clean room, tissue preparation and assay were carried out on a clean bench top on a sterile field, using sterile instruments and reagents. EGM, endothelial growth medium, as used in this study, contained 2% FBS, 10 ng/mL human EGF, 50 $\mu$g/mL gentamycin, 50 ng/mL amphotericin, and 12 $\mu$g/mL bovine brain extract. No hydrocortisone was added, despite its inclusion in the additives package supplied by Clonetics. Phosphate buffer saline (PBS) and EGM for tissue cutting and washing were kept on ice, in order to keep the tissues cold until they were sandwiched in Matrigel™. Medium was added shortly after the second layer of Matrigel™ had solidified, to prevent dehydration of the tissues. Treatments in EGM medium were kept at room temperature when added to tissues. In a Petri dish containing EGM medium, carotid arteries (one day on ice from abattoir) were gently trimmed of excess fascia, cut with scissors and splayed flat open. One mm$^2$ fragments were cut with a scalpel, using a pressing motion. Tissue fragments were washed in a Petri dish containing 1X PBS and were then ready to be placed into 48-well plates which contained 100 $\mu$L of reduced growth factor Matrigel™.

Angiogenesis Assay

100 $\mu$L of Matrigel™ was added to the 24 inner wells of a 48-well culture plate. 500 $\mu$L of 1X PBS was added to the outer wells to prevent evaporation. Tissue fragments were added, using forceps, on top of solidified Matrigel™ with the adventitia either up or down; orientation did not influence growth. An additional 100 $\mu$L of Matrigel™ was layered on top of the tissue fragment and allowed to solidify at room temperature. Five hundred microliters EGM +/– treatments were then added to each tissue/Matrigel™ sandwich. Sterile solutions were used. The concentration of DMSO did not exceed 0.5%. Plates were incubated in a humidified atmosphere of 5% $CO_2$ at 37° C., for two to three weeks. Medium (+/– treatments) was changed every three to five days. Sprouting was observed, under 34X magnification and visual inspection was maintained during the course of the incubation.

Imaging and Analysis

At the end of the two week incubation, samples were visualized with a microscope equipped with a 2X objective and digital images were generated with a Microimage video system equipped with a 0.5X high resolution coupler. Imaging was performed with the samples in their native state. TIF files of these images were quantitated using the image analysis software Image-Pro Plus. The measurements were taken in $\mu$m$^2$ using a calibration of 0.111 pixel/$\mu$m. The vessel body was subtracted out of the pixel calculation. A tracing was drawn around the outside perimeter of the vessel body to include all vessel sprouts. Care was taken not to allow samples to overgrow the confines of the microscopic field. By using uniform vessel fragments, this process may be more readily automated. Statistical analysis of the data was carried out and graphs were plotted using SigmaPlot 5 software.

The example above is intended to assist in a further understanding of the invention. Particular materials employed and conditions are intended to be further illustrative of the invention and not limiting of the reasonable scope thereof. Skilled artisans will be able to readily discern when alternative materials or conditions can be substituted.

Histological analysis using Factor VIII—related antigen (von Willebrand Factor) as an endothelial cell-specific marker identified these sprouts, which were consistent with endothelial cell morphology, supporting the system as a model of angiogenesis. This assay shows good reproducibility and eliminates animal to animal variation. The system is adaptable to other forms of angiogenic stimulation, ultimately making a variety of assays for angiogenesis available to laboratories of limited resources.

What is claimed is:

1. A method of analyzing the angiogenesis modulating effect of a compound, comprising the steps of:
   (a) incubating a sample that comprises of a fragment of porcine carotid artery with the compound;
   (b) generating images of the sample; and
   (c) quantitating the images to determine the extent of angiogenesis.

2. The method of claim 1, wherein the incubation of step (a) is in a humidified atmosphere of about 5% carbon dioxide at about 30° C. to about 40° C. for about 1 to 4 weeks.

3. The method of claim 1, wherein the incubation of step (a) is in a humidified atmosphere of about 5% carbon dioxide at about 37° C. for about 2 to 3 weeks.

4. The method of claim 1, wherein the incubation of step (a) is uses Matrigel™ as the matrix.

5. The method of claim 1, wherein the images generated in step (b) are digital.

6. The method of claim 5, wherein the digital images are quantitated in step (c) using image analysis software.

7. The method of claim 6, wherein the digital images are quantitated in step (c) using image analysis software and the vessel body is subtracted out of the pixel calculation.

8. A method of analyzing the angiogenesis modulating effect of a compound, comprising the steps of:
   (a) incubating a sample that comprises of a fragment of porcine carotid artery with the compound in a humidified atmosphere of about 5% carbon dioxide at about 37° C. for about 2 to 3 weeks;
   (b) generating digital images of the sample; and
   (c) quantitating the digital images to determine the extent of angiogenesis using image analysis software.

9. The method of claim 1 wherein the angiogenesis modulating effect is inhibition of angiogenesis.

10. A method of analyzing the angiogenesis inhibiting effect of a compound, comprising the steps of:
    (a) incubating a sample that comprises of a fragment of porcine carotid artery with the compound in a humidified atmosphere of about 5% carbon dioxide at about 37° C. for about 2 to 3 weeks in a Matrigel™ matrix;
    (b) generating digital images of the sample; and
    (c) quantitating the digital images to determine the extent of angiogenesis using image analysis software.

11. A kit for analyzing the angiogenesis modulating effect of a compound, comprising a fragment of porcine carotid artery in a medium with sufficient nutrients to allow growth of new vascular tissue.

* * * * *